United States Patent [19]

Trop et al.

[11] Patent Number: 5,800,485
[45] Date of Patent: Sep. 1, 1998

[54] COOLING CYLINDRICAL DEVICE FOR THERAPEUTIC TREATMENT OF HEMORRHOIDS

[75] Inventors: Moshe Trop, Brooklyn, N.Y.; Avraham Kushelvesky; Gedalya Mazor, both of Metar, Israel; Sergay Popov, Ofakim, Israel; Boris Baybikov, Mahale Edomim, Israel

[73] Assignee: Trop Life Ltd., Ofakim, Israel

[21] Appl. No.: 392,316

[22] Filed: Feb. 22, 1995

[30] Foreign Application Priority Data

Feb. 22, 1994 [IL] Israel ......................................... 108744

[51] Int. Cl.⁶ ............................................................. A61F 7/00
[52] U.S. Cl. ............................................................. 607/105
[58] Field of Search .................................... 607/104–405, 607/113–114; 128/884–885, 887; 604/907; 606/20–23, 25

[56] References Cited

U.S. PATENT DOCUMENTS

| 77,539 | 5/1868 | Schevenell et al. | |
|---|---|---|---|
| 149,872 | 4/1874 | Ludlow | 607/105 |
| 969,134 | 8/1910 | Cowie | |
| 3,496,942 | 2/1970 | Shipley | 607/105 |
| 3,939,842 | 2/1976 | Harris | |
| 4,240,436 | 12/1980 | Singleton | |
| 4,331,151 | 5/1982 | Golden | 607/105 |
| 4,638,806 | 1/1987 | Bartlett | 607/105 |
| 4,844,074 | 7/1989 | Kurucz | 607/105 |

*Primary Examiner*—Robert L. Nasser
*Assistant Examiner*—Ryan Carter
*Attorney, Agent, or Firm*—Lowe Hauptman Gopstein Gilman & Berner

[57] ABSTRACT

A cooling cylindrical insert device to aid in the removal of pain and for the therapeutic treatment of hemorrhoids and anal fissures. The device includes a hollow insert, finger or bulb contoured for insertion into the anus. At least one inlet and/or outlet opening is provided in the insert at its base, with one or two tubes connected to the openings. A container of cold liquid is provided connected to the inlet and outlet tubes. Thus, cold liquid is circulated from the container, through the inlet tube and inlet opening, through the cylindrical insert device, through the outlet opening and outlet tubes back into the container. A pump is provided to circulate the liquid.

21 Claims, 20 Drawing Sheets

COOLING CYLINDRICAL DEVICE FOR THERAPEUTIC TREATMENT OF HEMORRHOIDS

FIELD OF THE INVENTION

The present invention relates to a cooling cylindrical device for therapeutic treatment of hemorrhoids. More specifically, said invention relates to a cooling cylindrical finger adapted in its contour for insertion into the anus, wherein said cylindrical finger is cooled by cold water or ice or by expansion of gas or by thermoelectric cooler component.

BACKGROUND OF THE INVENTION

Commonly known as piles, hemorrhoids are varicose veins in the anal area. They are similar to the twisted and swollen veins that are frequently noticeable on a person's legs, especially in older women who have had several children. When these varicosities occur high in the anal canal they are referred to as internal hemorrhoids. Many people with internal hemorrhoids are unaware of their presence. External hemorrhoids are those near the anal opening; sometimes they prolapse and bulge outside the anus. When a person complains of having hemorrhoids, they are usually referring to the external type.

The most frequent cause of hemorrhoids is straining at stools, which is most likely to happen when a person is constipated, obese or pregnant. People with liver disease such as cirrhosis may also develop hemorrhoids due to increased pressure in the veins of the intestine.

Many people believe that hemorrhoids can be caused by sedentary occupations, sitting on hard, cold surfaces, prolonged standing, or diarrhea. These conditions are not responsible for hemorrhoids, but, can be causes of a condition called thrombosed external hemorrhoid. This is actually a hematoma or blood-filled swelling due to the rupture of an external hemorrhoidal vein. It follows a sudden increase in pressure within the vein and usually occurs after heavy lifting, coughing, sneezing, exercise, straining at stools, or giving birth.

Treatment is aimed at easing the symptoms. Stool softeners help reduce straining at the stool and so does loosing excess weight. A variety of creams and medications are available to soothe inflammation and itching but those containing cortisone should only be used if a physician advises them. Pregnant women should avoid any medications unless prescribed by the physician.

Surgery may be required in stubborn cases. One procedure involves ligation, or tying off the hemorrhoid with a rubber band to strangulate it. Internal hemorrhoids are sometimes treated by sclerotherapy, injecting of a chemical into them to cause fibrous tissue to grow and prevent blood flow. Cryosurgery uses liquid nitrogen or carbon dioxide to freeze the hemorrhoid. In a few cases, hemorrhoidectomy or removal of the entire hemorrhoid is necessary. This may be done with conventional surgery or with a laser.

Diagnosing hemorrhoids involves a physical examination, and a procedure called anuscopy is also needed to detect the presence of internal hemorrhoids. A small instrument is inserted into the rectum to allow the doctor to check for hemorrhoids and associated inflammation. Proctosigmoidoscopy, which also involves inserting an instrument higher up into the rectum, may be done to rule out other diseases.

Hemorrhoids may be present for years, with bleeding being the first symptom. They may come and go, flaring up during pregnancy or constipation. In many people they never become a serious problem. Eventually, hemorrhoids may prolapse and if not reinserted manually may protrude permanently, which can cause a discharge and irritate the skin. Long duration of hemorrhoids may lead to anaemia because of chronic blood loss.

Experts believe that more than 50% of the population has hemorrhoids. In a review of the records of 23,446 patients with hemorrhoids, it was found that 80% of the patients were between the ages of 30 and 60 years.

The anus, the opening at the lower part of the rectum through which bowel movement pass from the body, is warm, moist and richly endowed with sensory nerve receptors. These nerve endings register feelings of itchiness when they are mildly stimulated, and feelings of pain when the irritation is more intense. Thus, anal itching is often interspersed with pain.

Frequently, the itching is due to temporary, often trivial events, such as eating foods that cause irritation. Common offenders include red pepper and other hot spices. Atopic dermatitis which may be caused by an allergic reaction to perfumes and other chemicals in soaps, bubble baths, spays and even toilet paper, can cause intense anal itching. Infectious organisms such as the candidas fungus, or various bacteria also cause anal itching. Pinworms, which commonly infect children, cause intense itching. Diabetes and psoriasis also can cause itching.

Itching can occur if the anal area is inadequately cleaned after a bowel movement. Too much rubbing with toilet tissue also can cause it, and one brand or type of tissue may be irritating, while another is not. Tight clothing that encourage sweating and the growth of bacteria or fungi are common causes of anal itching, particularly in the summer.

Contrary to popular belief, hemorrhoids do not in themselves cause itching. The itching that many hemorrhoid sufferers experience is often due to hygienic practices, such as inadequate wiping, or to the medications used to relieve discomfort from the hemorrhoids themselves. In most instances anal itching is not dangerous. But it can be distracting and debilitating and needs to be relieved as soon as possible.

A wide variety of over-the-counter drugs are sold to relieve anal itching. Few have been shown to be safe and effective according to Food and Drug Adminstration criteria. Hydrocortisone creams and ointments (0.5%) are effective for itching outside the rectum, but should not be used inside. Anaesthetics such as benzocaine ointment or parmoxine hydrochloride, in cream or jelly form, also can be used in this way.

Commercial suppositories and ointments have no overall effect on hemorrhoids and itching because the hemorrhoids and the itching points are located under the skin or under, the membrane, and whatever is put on top of the skin or membrane can have little effect on what is under it.

There has been a long recognized need for a simple, inexpensive, non-toxic, self-administered device or procedure that has no possible harmful side effects or after-effects. Several attempts have been made, some of these goals have been achieved, but heretofore none has been entirely satisfactory for one or more reasons.

As long ago as 1868 Schevenell et al. in U.S. Pat. No. 77,539 proposed an instrument for treating piles or hemorrhoids involving a tapered hollow electrode of different metals to provide galvanic action when brought into contact with the body fluids, which was claimed to reduce the rectal inflammation. The electrode was to be inserted into the rectal cavity and held in place for several hours in order to achieve the asserted beneficial treatment. Optionally includable within the hollow electrode was a frozen substance. Apart from the prolonged length of required treatment, the other main deficiencies of the device were the need for cleaning and sterilization between uses and the likelihood that the metallic constituents would become toxic acids or salts when brought in contact with body fluids that would enhance, rather than diminish, the bodily disorder.

Another unsuccessful attempt was proposed by Cowie in U.S. Pat. No. 969,134 dated Aug. 30, 1910, who suggested the use of a hollow device, presumably of metal, having a removable screw cap so that crushed ice or other freezing, cooling, or heating medium could be employed. The device of Cowie, albeit some forty or more years after Schevenell et al. did not advance the technology, but rather had the same drawbacks and deficiencies as the proposal of Schevenell et al.

Other more recent efforts have been made to meet this long-felt need, but heretofore no one had devised or even suggested a conveniently packaged, self-administered, completely rectal insert for hemorrhoidal therapy.

Harris presented a proposal by U.S. Pat. No. 3,939,842 in 1976—a disposable rectal insert of plastic material chemically inert to body fluids encapsulating a freezable medium having a freezing point of about 0 degrees to 32 degrees Fahrenheit. The insert has a small bulbous end for rectal insertion which is collapsible upon melting of the medium and compensating dilation of the other enlarged reservoir end maintains constant inertial volume of the insert.

Another device was proposed by Singleman by U.S. Pat. No. 4,240,436 in 1980. It was a disposable perineal ice pack having an anatomical shape specially adapted for treatment of swelling and other disfunction of the rectal-vaginal pelvis region of female subject, composed of a flexible hollow synthetic material having a cold temperature storage medium therein, such as water, or other liquid freezable between 0 degrees to 32 degrees Fahrenheit, wherein said ice pack is specially contoured to compliment both the rectal and vaginal regions adaptable for use during post-operative surgeries or traumatic insults to the pelvic region.

The existing devices in comparison to the device according to the present invention suffer from the following defects:

1) The amount of heat the device can absorb in contact with live tissue is limited since the volume of cooling liquid is small (7 ml). Hence the useful period of application is corresponding small amounting to 2–3 minutes only.

2) The cooling rates of present devices are not controllable since they depend solely on the initial temperature of the freezer.

3) In most cases the cooling device is done in the domestic freezer usually containing food provoking negative association. Repeated freezing and defrosting could crack the walls of the insert and thereby would be dangerous to the soft tissue of anus and the rectum.

SUMMARY OF THE INVENTION

The present invention relates to a cooling cylindrical device for therapeutic treatment of hemorrhoids comprising a hollow cylindrical finger adapted in its contour for insertion into the anus, with inlet and outlet openings at its upper base, two tubes connected to said openings, and at least one tube is connected to a container for cold liquid flow. The liquid circulates from the container, through a tube, into the cylindrical finger and back through the outlet opening and the second tube to the container enabled by a pump connected to the container or back to another container operated simply by gravity.

The terms "cylindrical device" "cylindrical finger" or "cylindrical insert" in this invention are not strict geometrical definition with round cross section but can be with variation such as oval or eliptic.

The terms "insert" or "finger" in this invention are identical and function as an anal cooling element.

Prior to the invention herein, there has been no comparable thermally controlled continuous operated rectal insert for treatment of hemorrhoids. The device according to the present invention is thermally controlled, easily operated either by the physician or by the nurse or even by the patient himself. Said device applies uniform and continuous cooling inside and outside the rectum and the anus. The optimal temperature is achieved by adjusting the flow of cold water via the cylindrical insert. The cold temperature above the freezing point of water is according to the convenience of the patient thereby preventing the possibility of injury by a frostbite or by drastic hypothermal conditions.

A systematic repeated use of the present insert will not only remove the pains and itching, but may also shrink the swollen blood vessels.

In order to extend the duration of treatment period and to maintain control on the temperature during application the following modifications were made:

1. Inlet and outlet ducts to the cylindrical "finger" used to cool the inflamed tissue, were added to enable cooling liquid to be circulated continuously.

2. A thermally insulated container of about 0.5–1.0 liters were employed to hold the low temperature cooling solution.

3. A pump to circulate the cooling solution through the cylindrical finger via inlet and outlet ducts, was added.

4. A flow valve to adjust the low rate and to control the temperature.

Alternatively, the 2) and 3) are simplified by using a plastic container, as used for medical infusions to hold the cooling solution and circulating the cooling liquid by means of flowing by gravity. In both cases the liquid is cooled separately, for example, by using ice cubes or crushed ice or by cooling the whole cylinderical device in a home freezer or refrigerator.

Alternatively the cylindrical insert is not hollow, but rather is built of a full section made of a metal like stainless steel, aluminium, titanium, nickel, iron coated with chrominium, gold alloys, or copper, connected to the container made of metal as well, or of plastic. The container is filled by peace of ice, crushed ice, or ice-cold water, or other cold liquid. The cylinder is cooled by conductivity of heat towards the cold container.

A completely different approach to achieve continuous cooling is to construct the finger of a solid metal and to cool it by using a thermoelectrically cooler attached to it. This alternative is also part of the present invention and has the advantage of the cooling being an integral part of the device.

The present invention further provides a hollow cylinder made of metal or plastic cooled by letting compressed gas to expand inside using a compressed gas or liquid gas tank and a valve to regulate the release of gas and a hose leading the released gas into the hollow of the cylinder where it expands and runs off.

The following embodiments of the device according to the present invention are demonstrated below:

1. Cylinder cooled by water flowing due to active pumping;
2. Cylinder cooled by water flowing due to gravitation;
3. Cylinder cooled by a thermoelectric cooler component;
4. Cylinder cooled by attachment to a compartment of ice cold water.
5. Cylinder cooled by expansion of gas.

DETAILED DESCRIPTION OF THE INVENTION

The present invention will be further clarified and exemplified by description of the preferred embodiments of the present invention. These preferred and alternative embodiments are illustrated in FIGS. 1–19 and do not intend to limit the scope of the invention.

Figure 1:
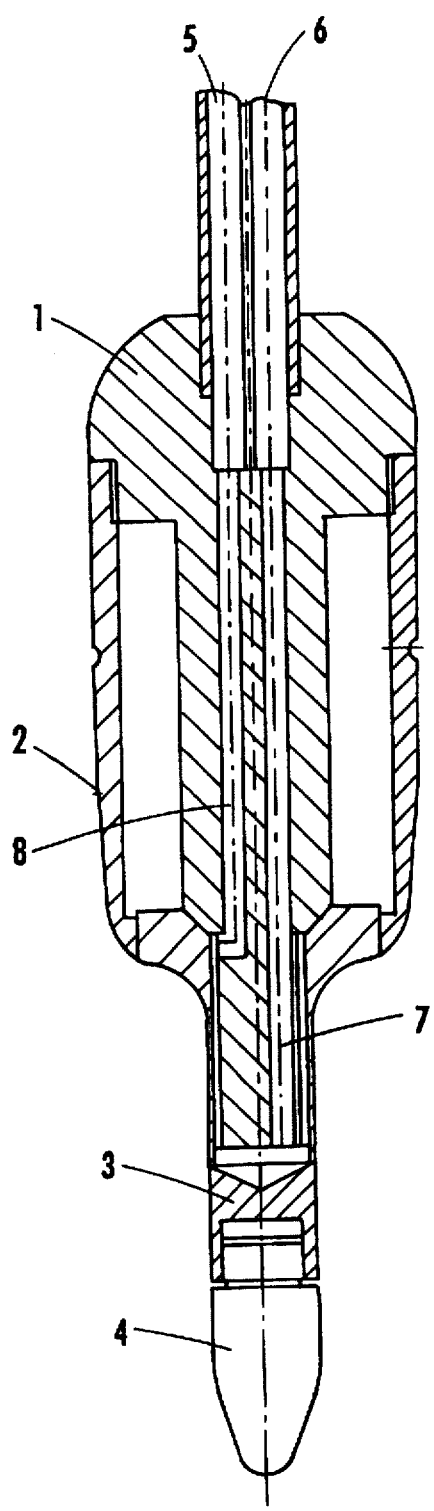
FIG. 1 is a cross-sectional view of the cylindrical insert device of the present invention.

FIG. 1—describes a cylindrical insert device consisting of a plastic, stainless steel, or other metallic cap (1) with an outer diameter of 23–40 mm, adjusted to fit the edge of the plastic, aluminium, copper, titanium or stainless steel hollow body (2); a plastic, aluminium, copper, titanium, nickel, chrominium coated iron, gold alloy or stainless steel cylindrical hollow insert tube (3) having a 10–14 mm outer diameter and a 9–13 mm inner diameter and 40–90 mm length, ending with a plastic, aluminium, copper, titanium or stainless steel full sectional uncooled tip (4). Two openings (5) and (6) and two plastic tubings (7) and (8) connected to said openings serve as inlet and outlet for circulation of cold water from the cooling container into the cylindrical insert and back to the cooling container. The insert is equipped with a disposable rubber elastic silicon covers for hygienic use.

Figure 2:
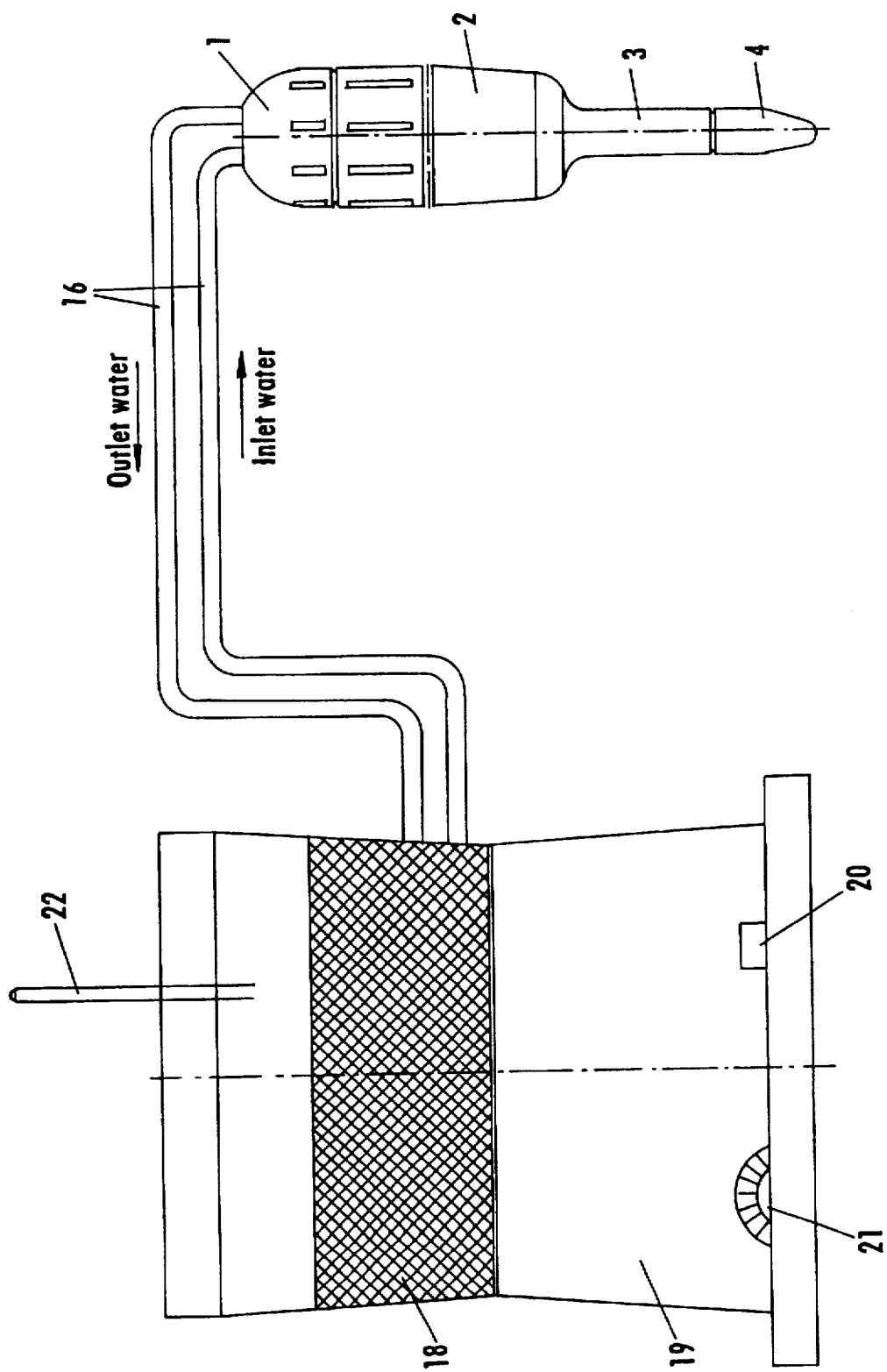
FIGS. 2, 3 and 4 are schematic representations of alternate embodiments of the cooling system for the cylindrical insert device.

FIG. 2—illustrates the whole system of the cylindrical insert cooled by pump-driven ice cold water.

The device is composed of the following parts (FIG. 2):
1. Cylinder (3) as shown in FIG. 1.
2. Two tubes (16) of plastic for circulation of water from the cooling container (18) to the cylinder and back to the cooling container.
3. Cooling container (18) of 100 to 1500 ml, holding iced water.
4. Pump (19) linked to the cooling container driving about 5–70 l/h.
5. On and off switch (20) and pressure regular (21).
6. Thermometer (22) for measuring cold water temperature.
7. Disposable covers of the cylinder.

By switching the on/off button and adjusting the required flow, the pump draws water out form the cooling container through the plastic tube to the cylinder.

The patient inserts the cylinder into the anus for a period of time convenient for him. Due to temperature gradient, heat will be quickly conducted from the surrounding tissue (hemorrhoids) to the cold water in the cylinder. The heat is transferred outside the cylinder by the second plastic tube, in which water flows back to the cooling container.

The advantages of the instrument described in FIG. 2 are as follows:

1. The instrument cools the hemorrhoid tissue in a continuous way, up to half an hour or more;
2. the temperature may be controlled and adjusted by the flow regulator;
3. the cylinder has longer life time;
4. the instrument may be used also for external hemorrhoids.

Figure 3:
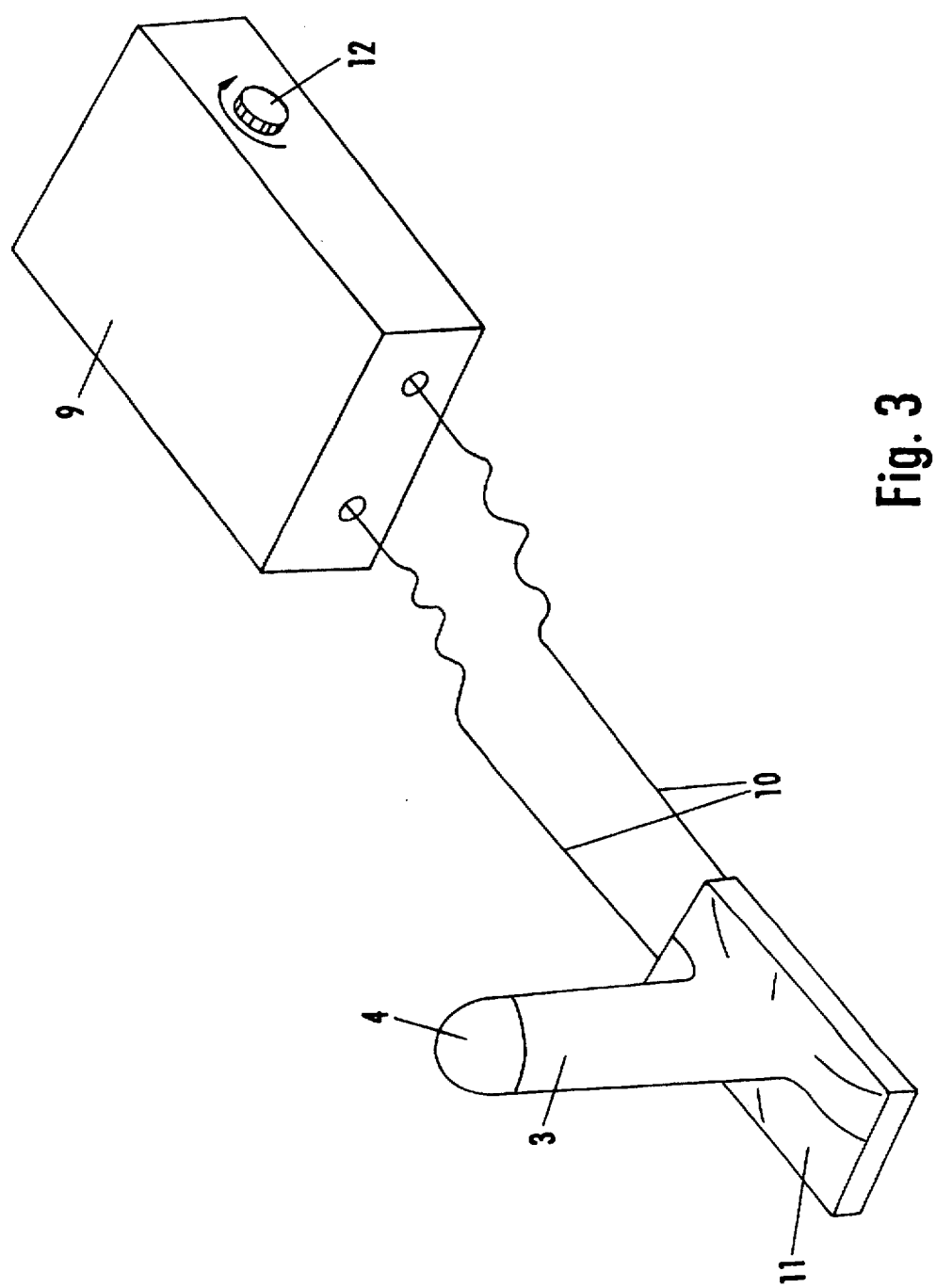

FIG. 3—illustrates a cylindrical insert cooled by a thermoelectric cooler component.

Its full section is made of stainless steel, titanium, copper, aluminium, nickel, chrominium coated iron, gold alloy or other metal, while its upper part is a cylinder preferably having a 10–14 mm diameter, its length is between 20–70 mm for treatment of internal hemorrhoids and between 10–30 mm for treatment of external hemorrhoids. The cylinder presented is made of one piece of stainless steel, titanium, copper, or aluminium, while its bottom base is square, eliptic or round with dimensions adjusted to those of the thermoelectric component.

The device is composed of the following parts:
1. Power supply (9) with 0–10 V voltage and 0–4 A.
2. Electric wires (10).
3. Cylinder (3) ending with an uncooled plastic tip (4).
4. Thermoelectric cooler component (11)—25 W–200 W.
5. On/off switch and voltage regulator (12).
6. Disposable covers for the cylinder for hygienic use.

By switching on and by adjusting the required voltage, the temperature of the cold side of the thermoelectric cooler component is selected. Due to the contact between the base of the cylinder and the thermoelectric cooler component, the cylinder is cooled to the required temperature.

The patient will insert the cylinder into the anus for a period of time convenient for him. Due to the temperature gradient and to the heat conductivity of the cylinder, the heat will be quickly conducted from the hemorrhoids to the cylinder. This heat will be transferred outside the cylinder to the hot side of the thermoelectric component and from there to the surroundings.

The advantages of the device described in FIG. 3 are as follows:

1. the instrument cools in a continuous way;
2. the temperature may be adjusted by voltage regulator;
3. longer life time of the cylinder;
4. the instrument may be used for external hemorrhoids as well as for internal ones;
5. reasonable price in relation to its efficiency.

Figure 4:
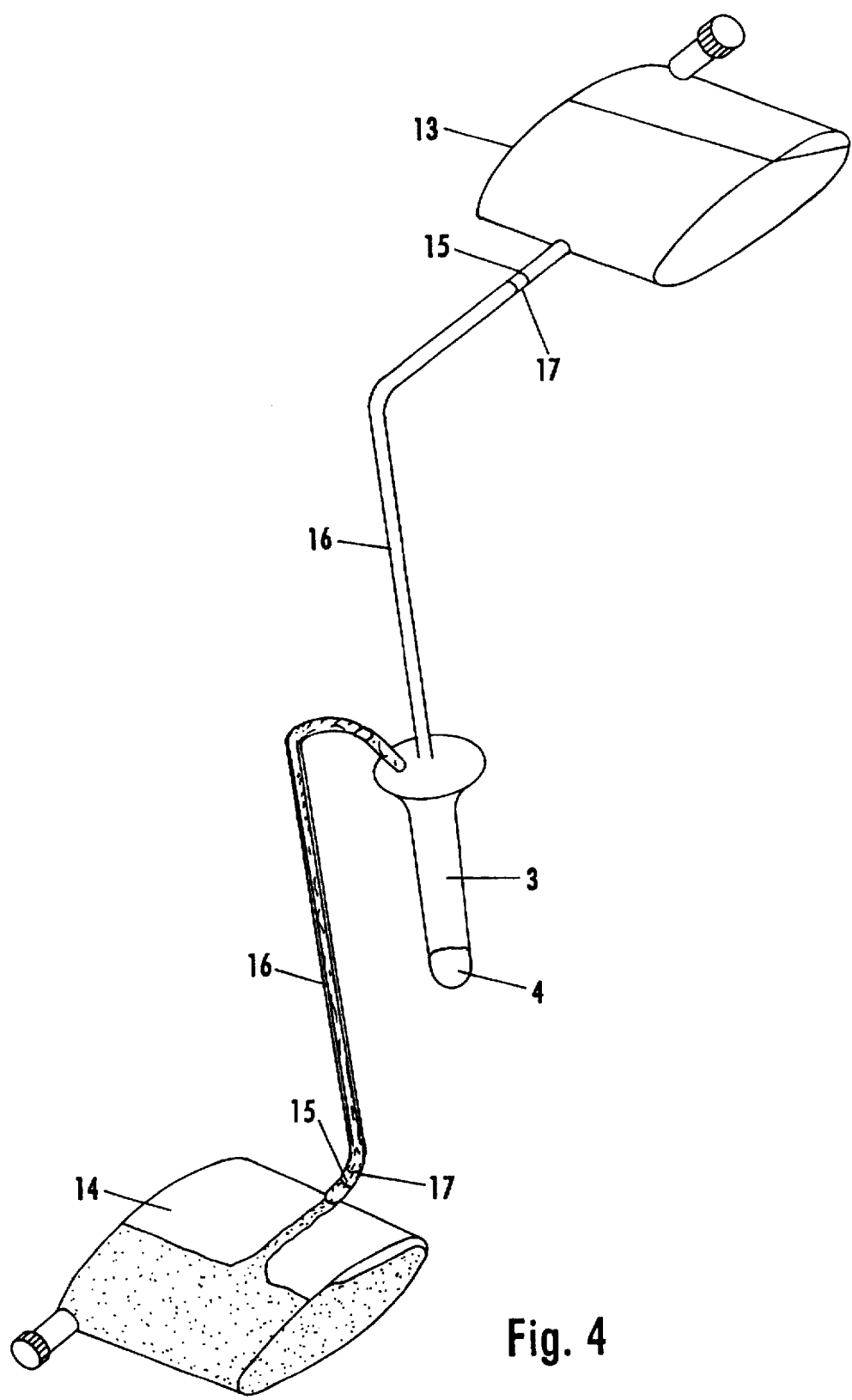

FIG. 4—describes a cylindrical insert cooled by gravitationally forced ice cold water.

The instrument is composed of the following parts: Two containers made of polyethylene with 500 ml to 2,000 ml; a container of cooling water (13) and a container of the used water (14); Two valves (15); Two plastic tubings (16) leading water from one container to the cylinder (3) ending with an uncooled tip (4) and from the cylinder to the second container; Cylinder (3); Two joints—(17) connecting the containers to the tubings; and disposable covers for the cylinder.

The two containers are placed at different heights of 20–50 cm (thereby adjusting the flow and the temperatures) in accordance with user's convenience; cold water will flow by gravitation from the container via the cylinder to the other container.

The patient will insert the cylinder into the anus for a period of time convenient for him; due to temperature gradient, heat will be quickly conducted from the surrounding tissue (hemorrhoids) to the cold water in the cylinder. This heat is conducted outside the cylinder to the other container. After the upper container is empty (approximately in 10–30 minutes), it will be necessary to change the places of the container.

The advantages of the instrument described in FIG. 4 are as follows:

1. the instrument cools in a continuous way and not limited in time;
2. temperature can be adjusted by the patient;
3. low price;
4. the instrument may be used for external hemorrhoids as well as for internal ones;
5. prolonged service life of the cylinder.

Figure 5B:
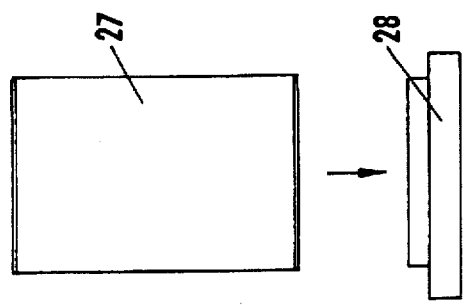
FIG. 5B is a cross-sectional view of a third embodiment of the cylindrical insert device.
Figure 5A:
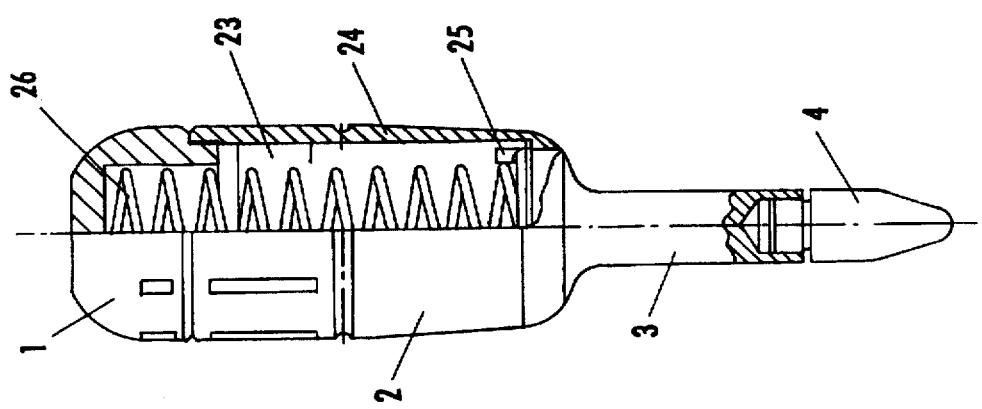
FIG. 5A is a cross-sectional view of a second embodiment of a cylindrical insert device.

FIG. 5a—illustrates a cylindrical insert cooled by attached container filled by iced water, or by a piece of ice or by crushed ice.

The device is composed of the following parts:

1. An aluminium, stainless steel, titanium, or other metal not hollow cylindrical insert (3) preferably 12.7 mm in diameter, 70 mm length, and ending with a tip (4). The plastic or rubber "penetrator tip" is installed in the fore end of the "cooling element", for easy and convenient insertion of the device, and for stabilizing the device while in use. The thermal insulation properties of the "penetrator tip" prevents unwanted cooling of healthy tissues beyond the hemmorrhoids.
2. The cylinder is connected to a cup like aluminium, stainless steel, titanium, other metal or plastic compartment (23) having 50–300 ml internal volume. That compartment is filled by ice or by ice cold water. The compartment is covered by sponge polyurethane insulation or any other plastic insulation 0–4 mm width (24). The inside of the compartment is equipped with a built in piston (25) and a spring (26) connected to the cap (1) which press the ice toward the front walls of the compartment. Screwed cap (1) of the compartment made of layers of aluminium, stainless steel, titanium or plastic coated by sponge polyurethane and a disposable thin plastic cover used for cover of the cylinder.

FIG. 5b—illustrates a modified device equipped with a plastic cylinder open in both sides (27). That cylinder hold an ice and located inside the compartment (23) and kept in contact with the flat side of the base of insert cylinder (3).

The way that plastic cylinder (27) is filled with ice is by tighten its open side onto plastic cylinder base (28) filling it by tap water freezing it and seperating it from the base (28). The patient adds ice cold water into the compartment, and covers it tight. The cylinder cools immediately. The patient inserts the cylinder into his anus.

There can be a variation of the insert illustrated in FIG. 5a. The variation is that the metal insert is coated by a layer of plastic.

The advantages of the device described in FIG. 5a is as follows:

1. the cylinder has continuous cooling;
2. the cylinder has a long life;
3. the cylinder is fitted for internal and external hemorrhoids;
4. it is inexpensive.
5. it is easy to use.

Figure 6:
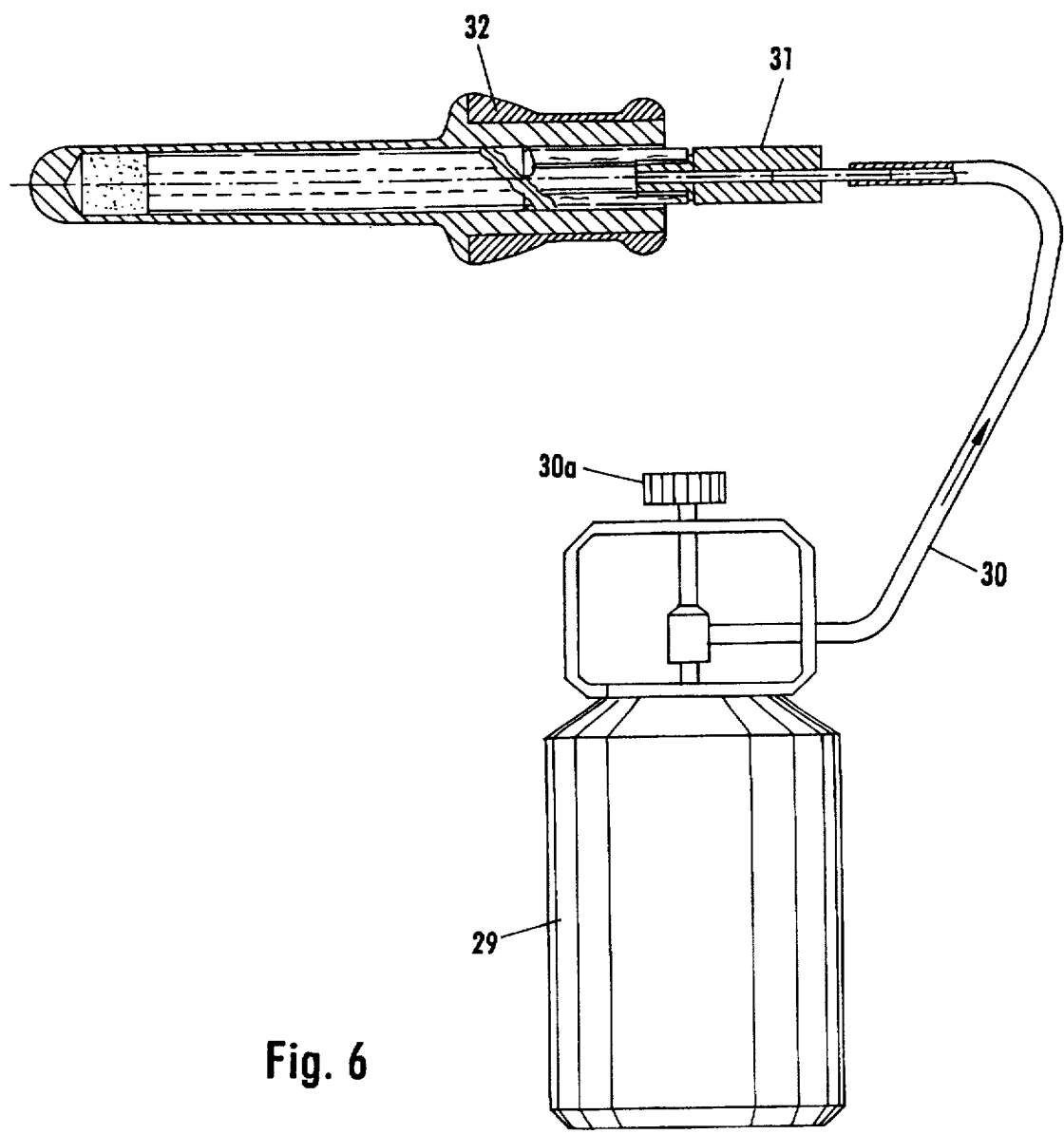
FIG. 6 is a view of an alternate embodiment of the gluing system for the cylindrical insert device.

FIG. 6—illustrates the cylinder (2) cooled by gas expansion. The device is composed of the following parts: a container of pressed gas such as CO2, Freon, air or N2, at pressure of 50–120 atm., (29). The gas is released via control valve (30a) which can be adjusted manually to release the necessary quantity of gas at the cylinder (3). The gas flows through an insulated plastic tubing (30). The cylinder is made of aluminium, copper, stainless steel, titanium or alloys thereof or plastic. The inner diameter is 1–10 mm, the outer diameter is 4–13 mm. The cylinder is equipped with a connection plug (31) made of plastic, aluminium, copper, or stainless steel to let the gas entering the cylinder where it expands in, and insulation cover (32) to hold the cooled cylinder. The patient inserts the cylinder into his rectum. The patient then turns the knob of the valve to get an appropriate gas flow in order to obtain the optimal temperature to cool the tissue, and hold it in this position for 5–30 minutes according to the physician's direction.

Figure 7A:
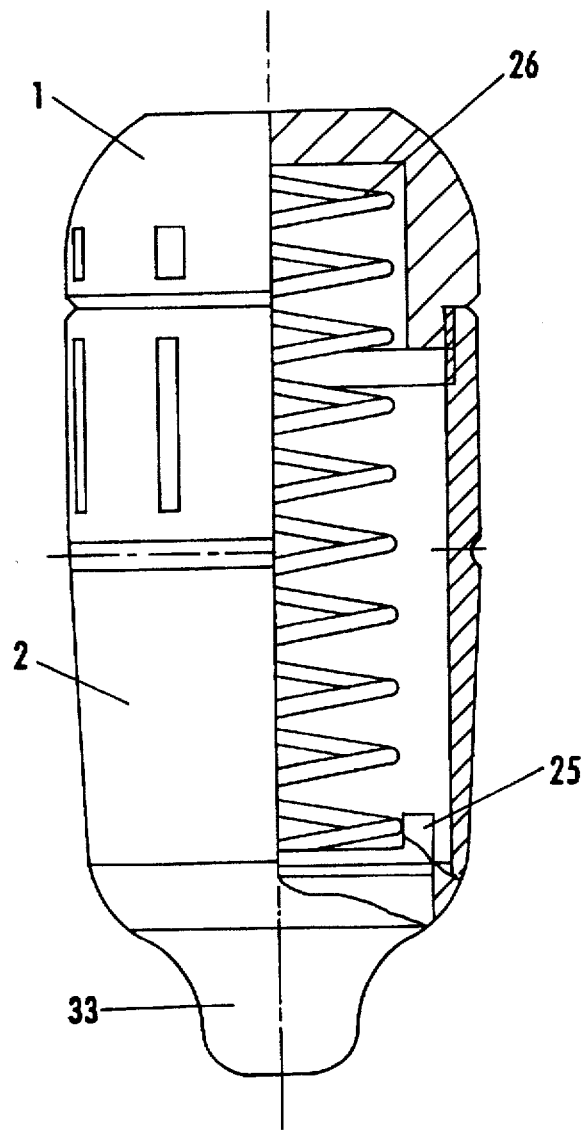
FIG. 7A depicts modification of the cylindrical insert device of FIG. 5.

FIG. 7a—describes a cooling external hemorrhoids treatment device simmilar to that described in FIG. 5. The only one variation is that it has an aluminium, copper, stainless steel, titanium or alloys thereof bulb (33) 5–20 mm length. That bulb is not ending with a tip and it is intended to touch the opening area of the anus.

This bulb could be coated with a layer of plastic.

Figure 7B:
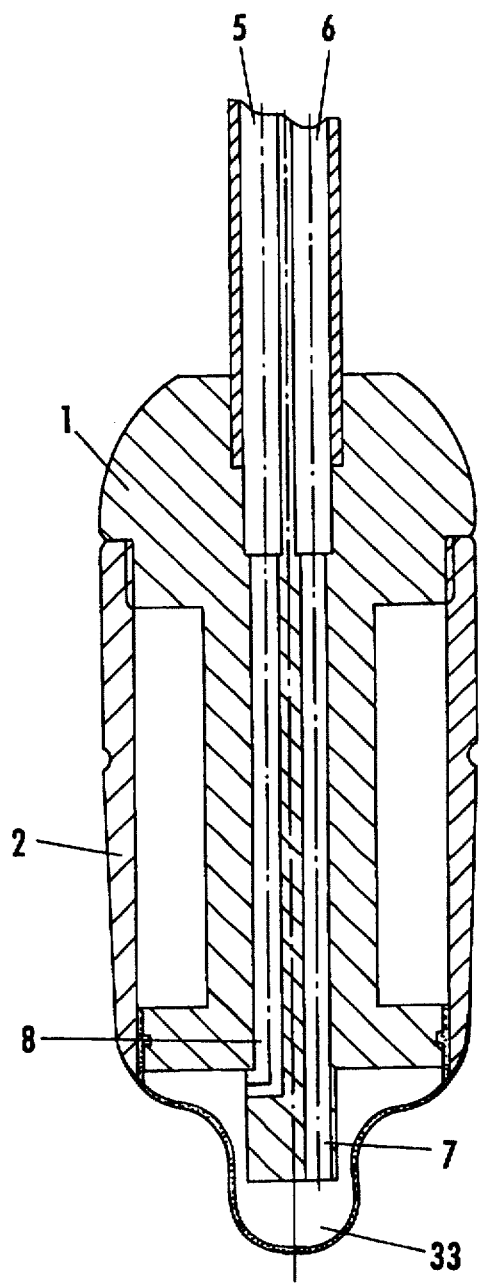
FIG. 7B is a cross-sectional view of another embodiment of the cylindrical insert device.
Figure 8D:
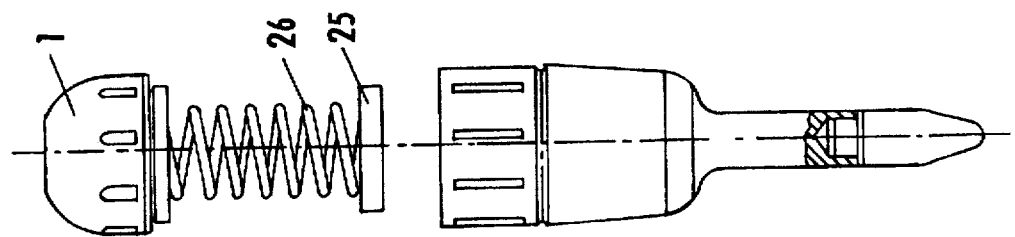
FIG. 8 illustrates the steps of using the cylindrical insert device of FIGS. 5A and 5B.
Figure 8C:
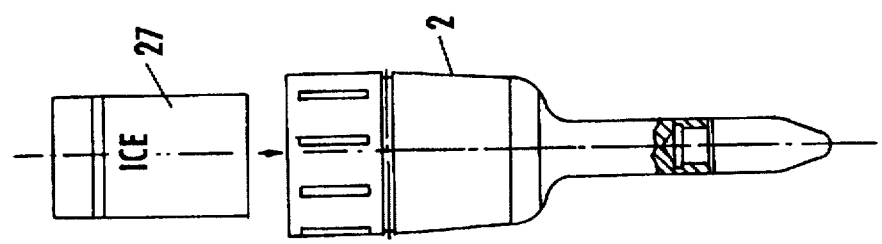
Figure 8B:
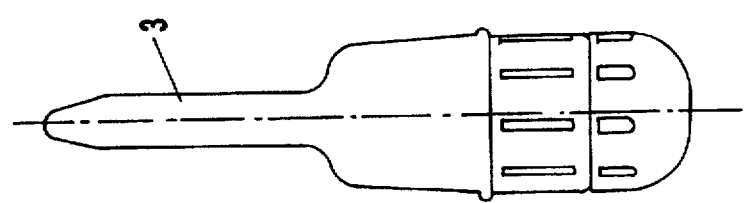
Figure 8A:
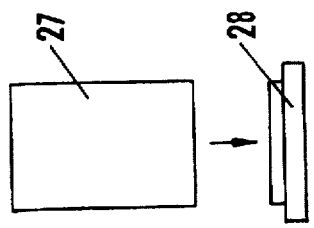

FIG. 7b—describes a cooling external hemorroids treatment device consisting of a plastic, stainless steel, or other metallic cap (1) with an outer diameter of 23–40 mm, adjusted to fit the edge of the plastic, aluminium, copper, titanium or stainless steel hollow body (2); a plastic, aluminium, copper, titanium, nickel, chrominium coated iron, gold alloy or stainless steel bulb (33) having 5–20 mm length. That bulb is not ending with a tip and it is intended to touch the opening area of the anus. Two openings (5) and (6) and two plastic tubings (7) and (8) connected to said openings serve as inlet and outlet for circulation of cold water from the cooling container into the cylindrical insert and back to the cooling container.

Disposable, sterile prophylactic covers are provided with the all devices (in all figures), for hygienic and anesthetic use. The prophylactic covers conform in shape to the cylinder (3) or to the bulb (33), and are lubricated, for convenient use.

FIG. 8—illustrates the steps of using the cylinder of FIG. 5:

1. Put the cylinder (27) onto its base (28) and tighten them together. Fill it with water and leave in freezer to freeze.
2. Cover the cylinder with the sterile prophylactic cover.
3. Seperate the cylinder (27) from its base (28) and insert it with the peace of ice in it into the compartment.
4. Screw the cap (1) with its spring (26) inside by pressing it on the ice packed in the cylinder (27).
5. Lie in bed on your left side role yourself in fetal position with your knees close to your head.

6. Insert the cylinder into your anus.
7. Hold it there for 10 minutes.
8. Take off the cylinder and discard the prophylated cover.

EXPERIMENTS AND RESULTS
Simulation of the Human Body

FIG. 9–12—illustrate curves of change in the temperature versus time using the various kinds of cylindrical inserts.

Figure 9:
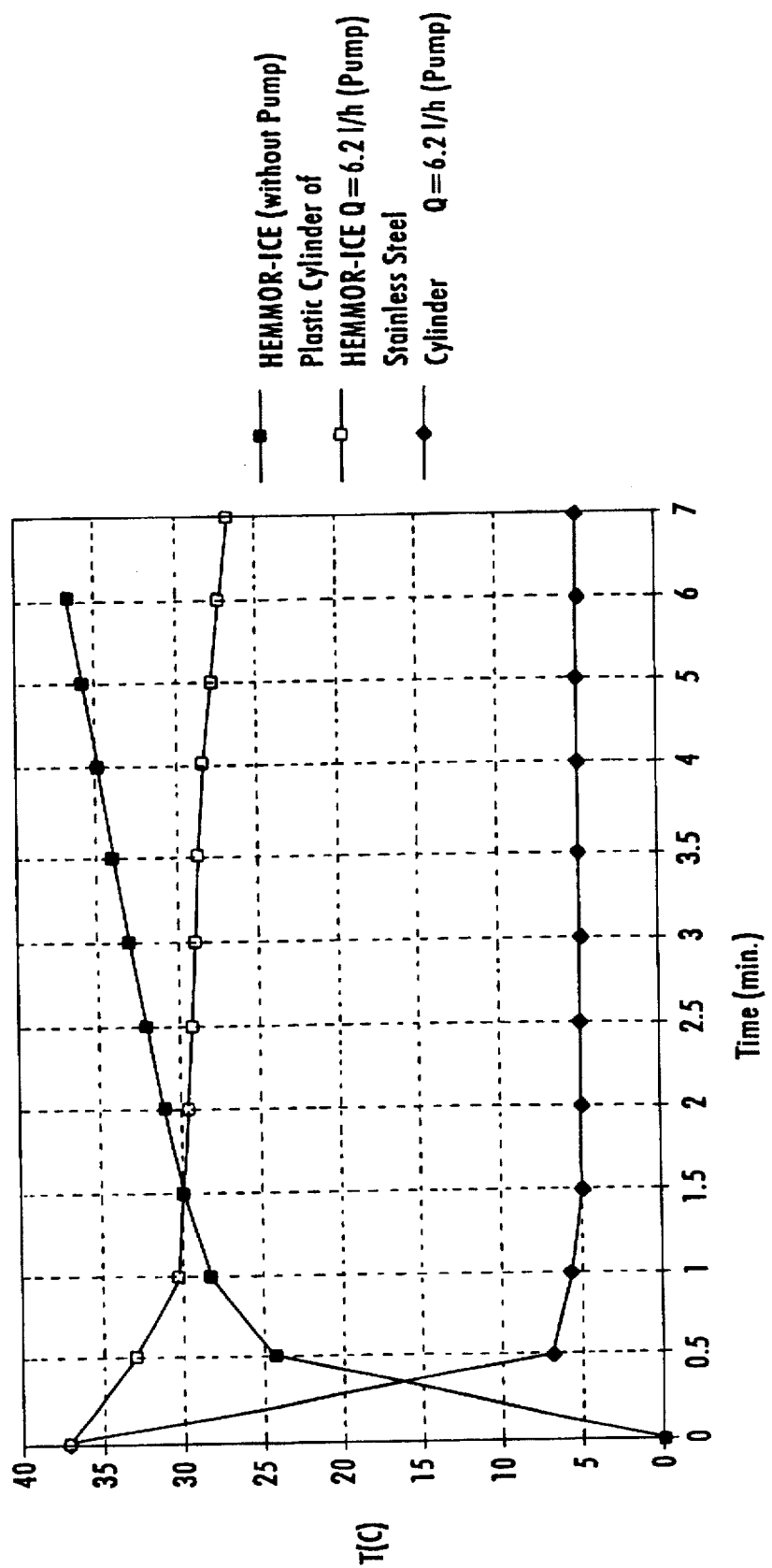
FIGS. 9–12 illustrate curves of change in the temperature versus time using various embodiments of cylindrical insert devices.
Figure 10:
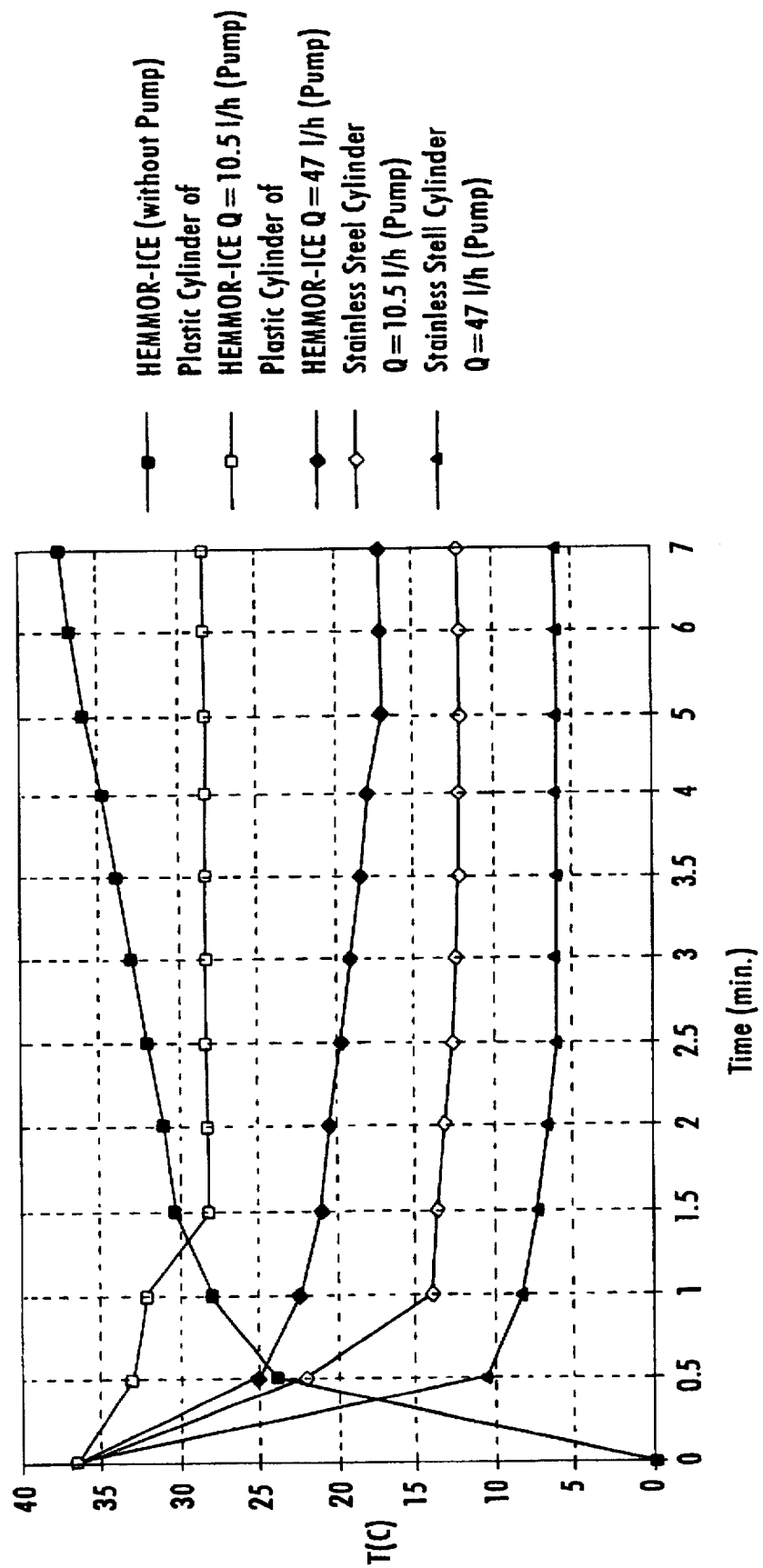

A plastic sponge dipped in a water bath at 37 degrees centigrade served for simulation of human rectal environment. A hollow cylinder was inserted into the sponge and ice-cold water was fed into the cylinder. The water was pumped by a small pump via plastic tubings and the temperatures were measured both inside the cylinder and on its outside walls within the sponge. The temperature values at one minute intervals were recorded at different flow rate of water. The results are shown in FIG. 9.

Trials with Animals

A female sheep 5 months old was used as a live model. One thermocouple probe was placed inside the cylinder, and a second one was attached to its outside wall inside the rectum of the sheep 4 cm deep. The pump was turned on, and the temperature values were taken at one minute intervals. A commercial "Hemmoride" cylinder was tried for comparison. The results are presented in FIG. 10.

Figure 11:
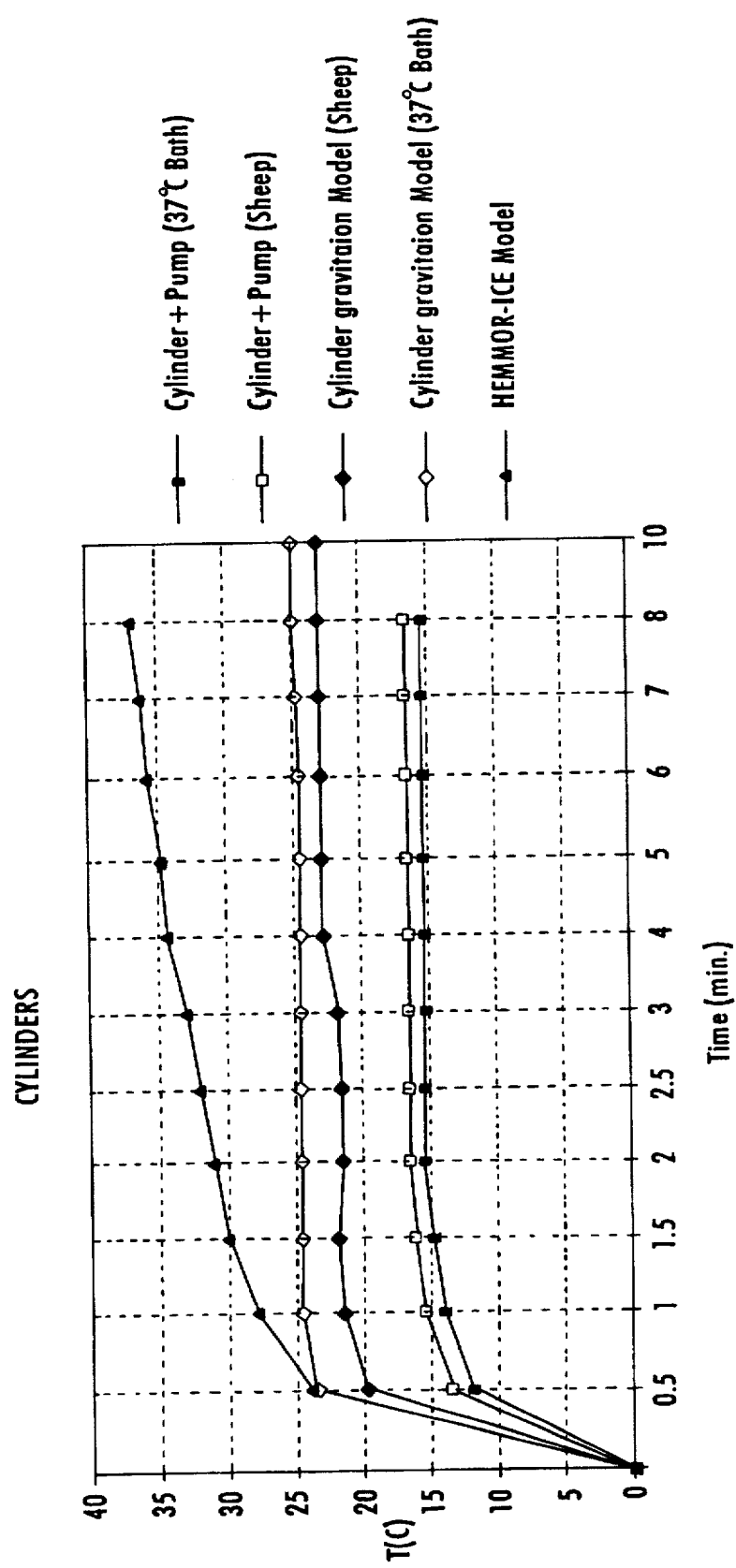
Figure 12:
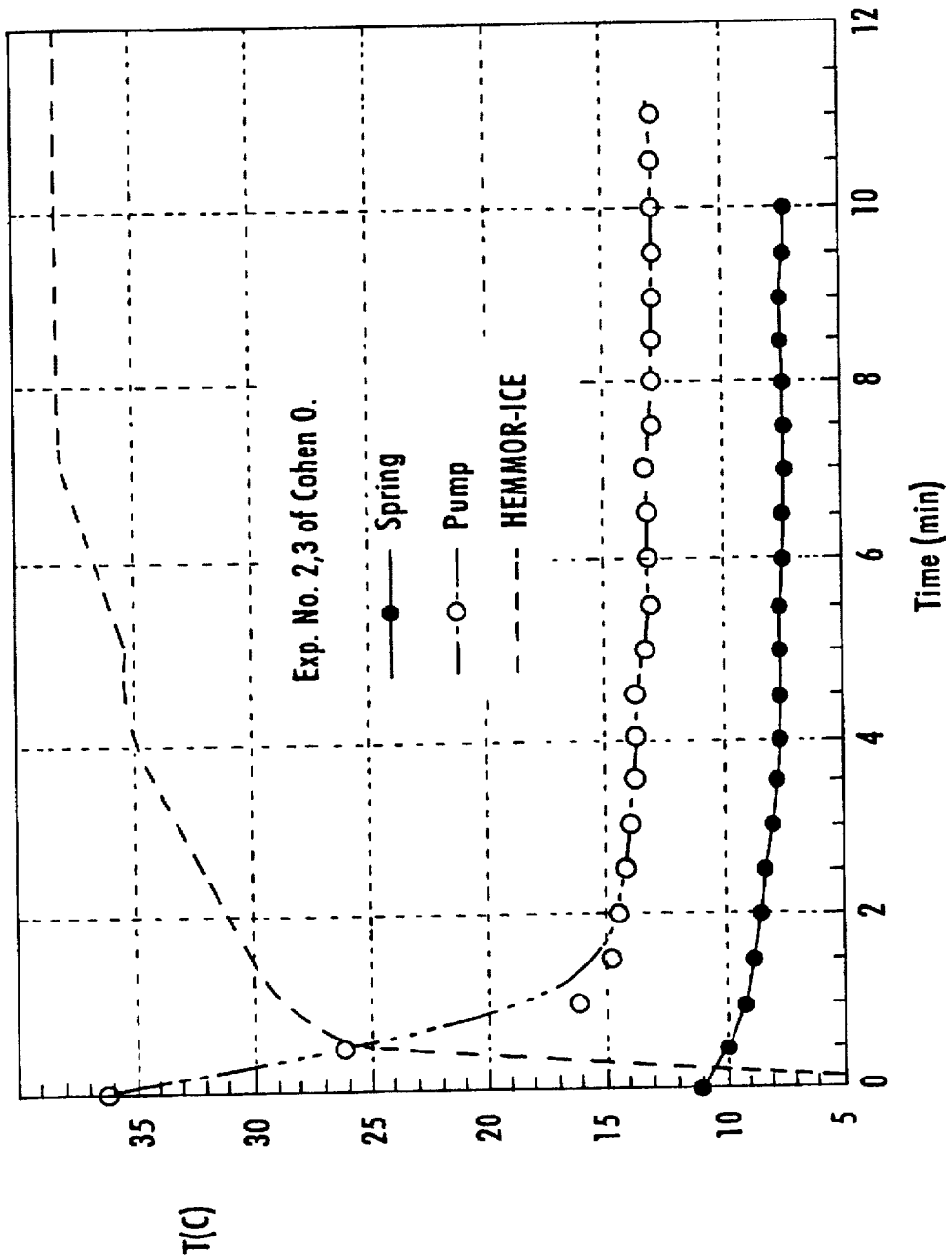
Figure 13:
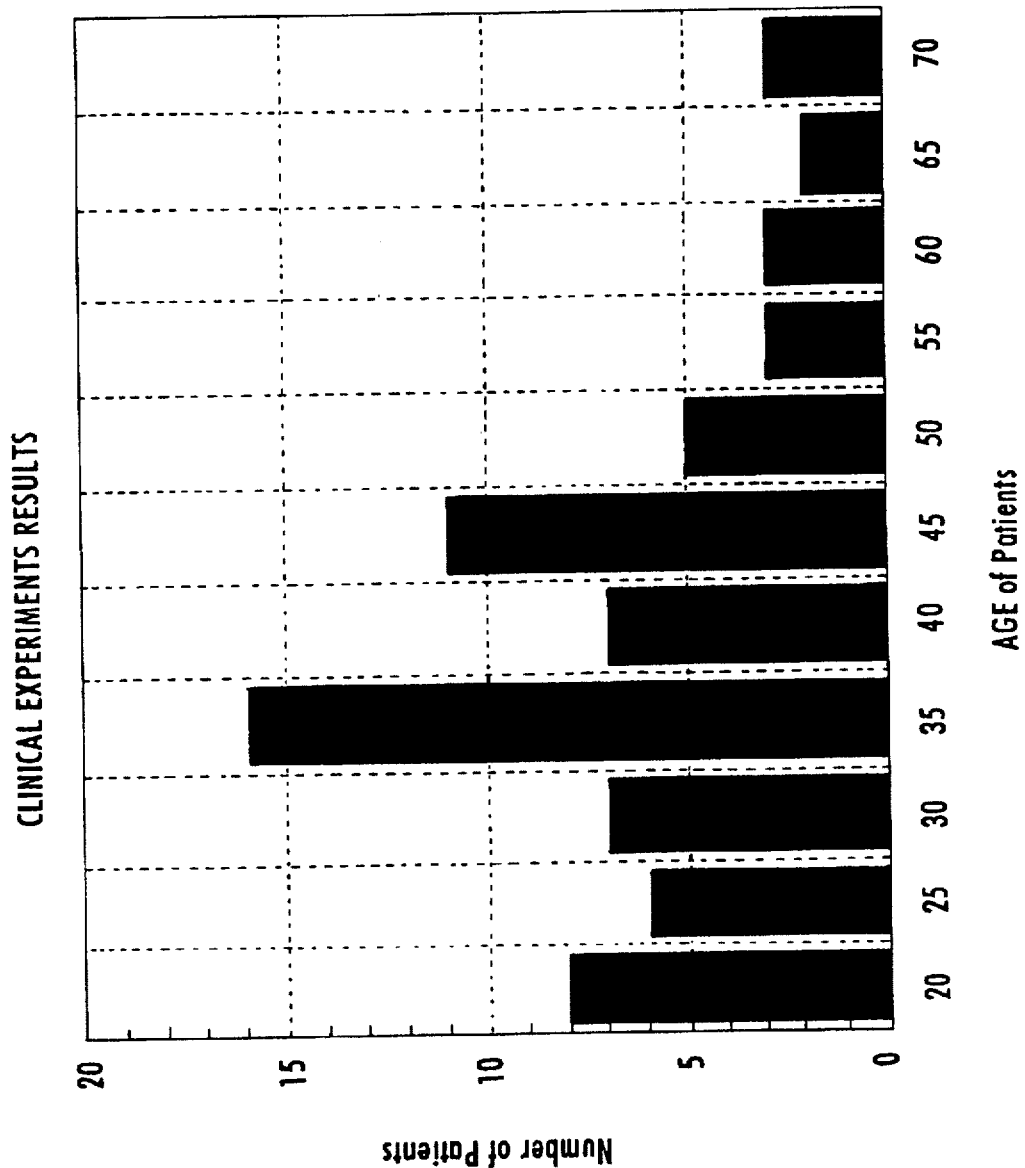
FIGS. 13–19 summarize the results of clinical experiments.
Figure 14:
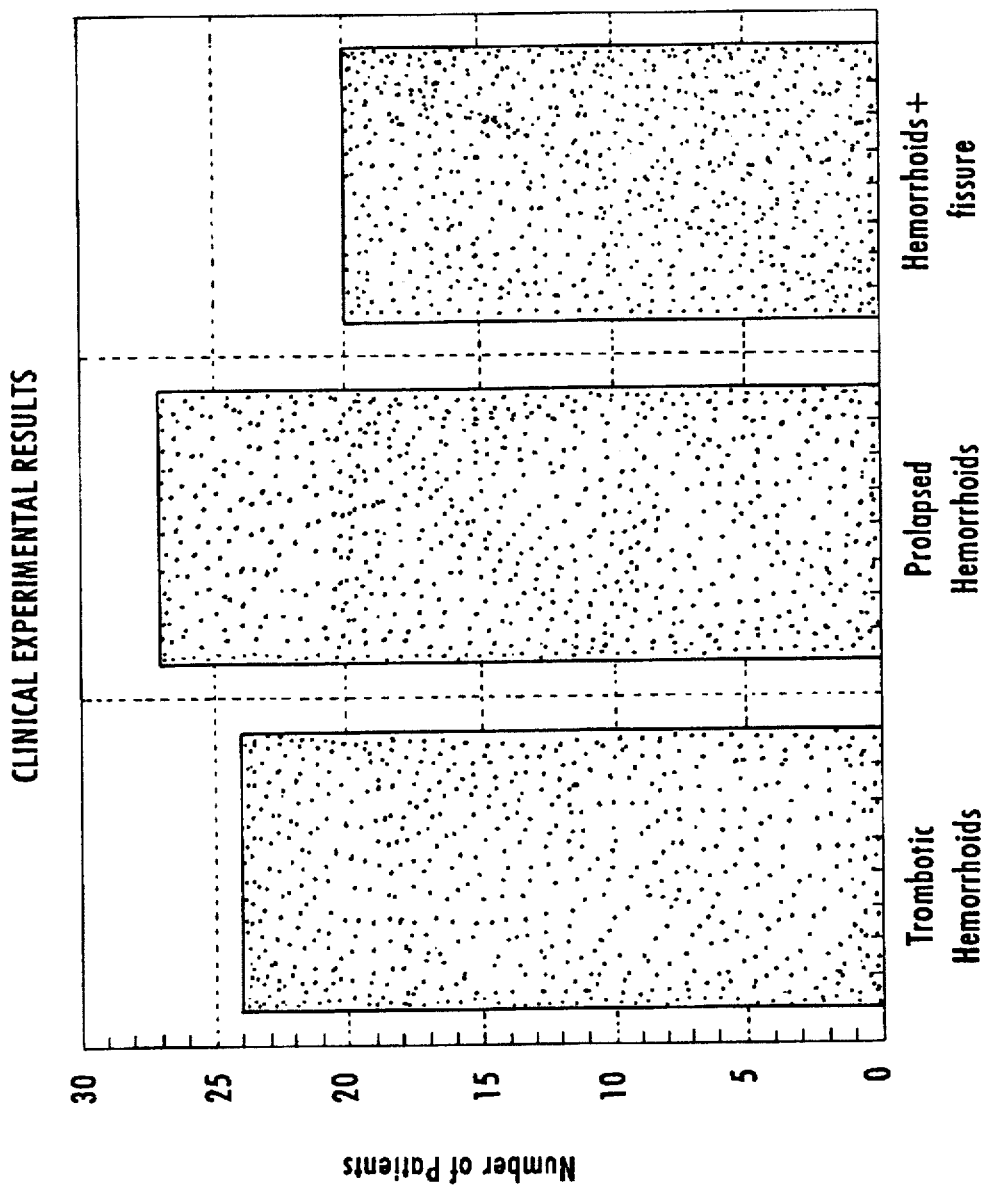
Figure 15:
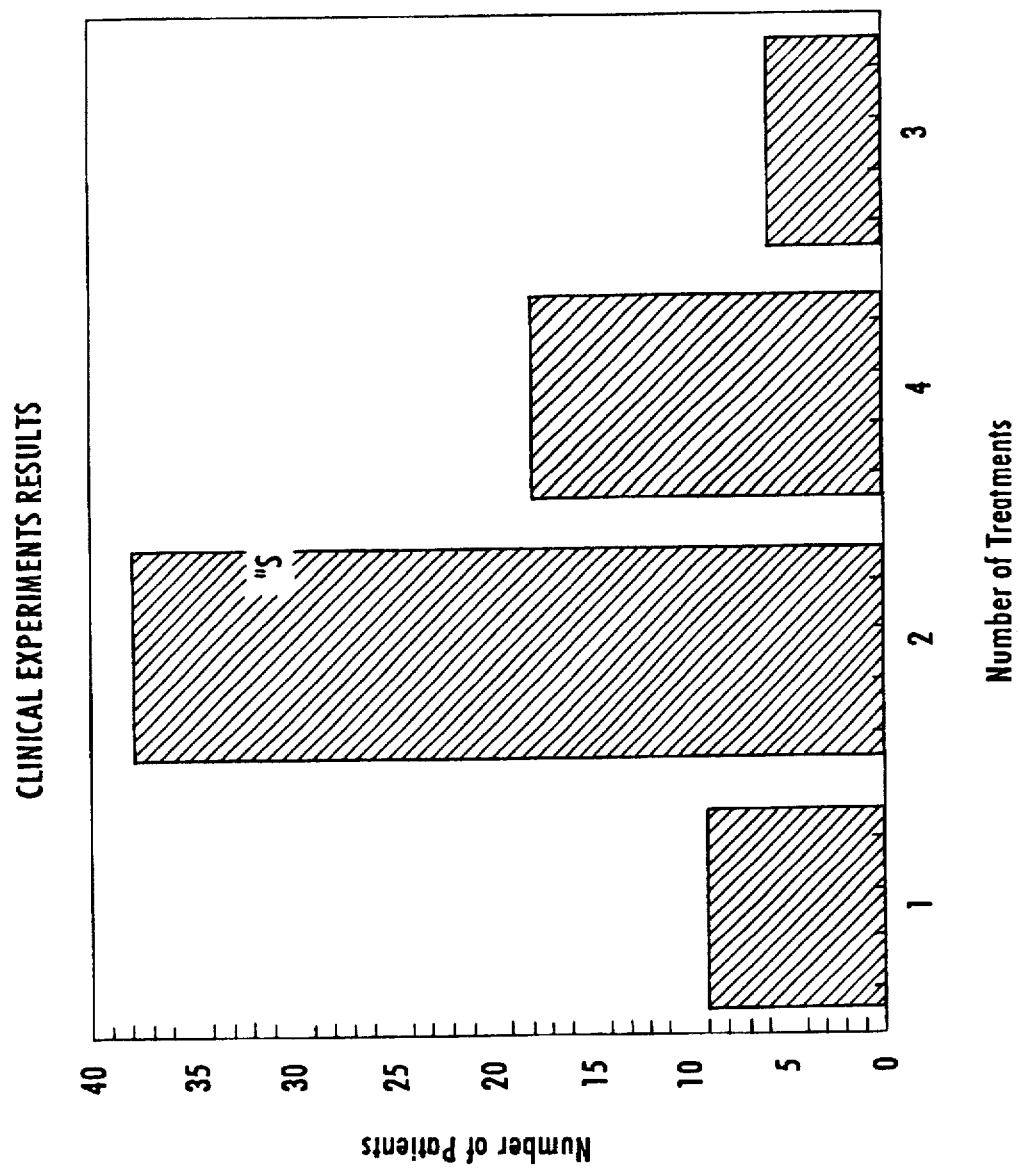
Figure 16:
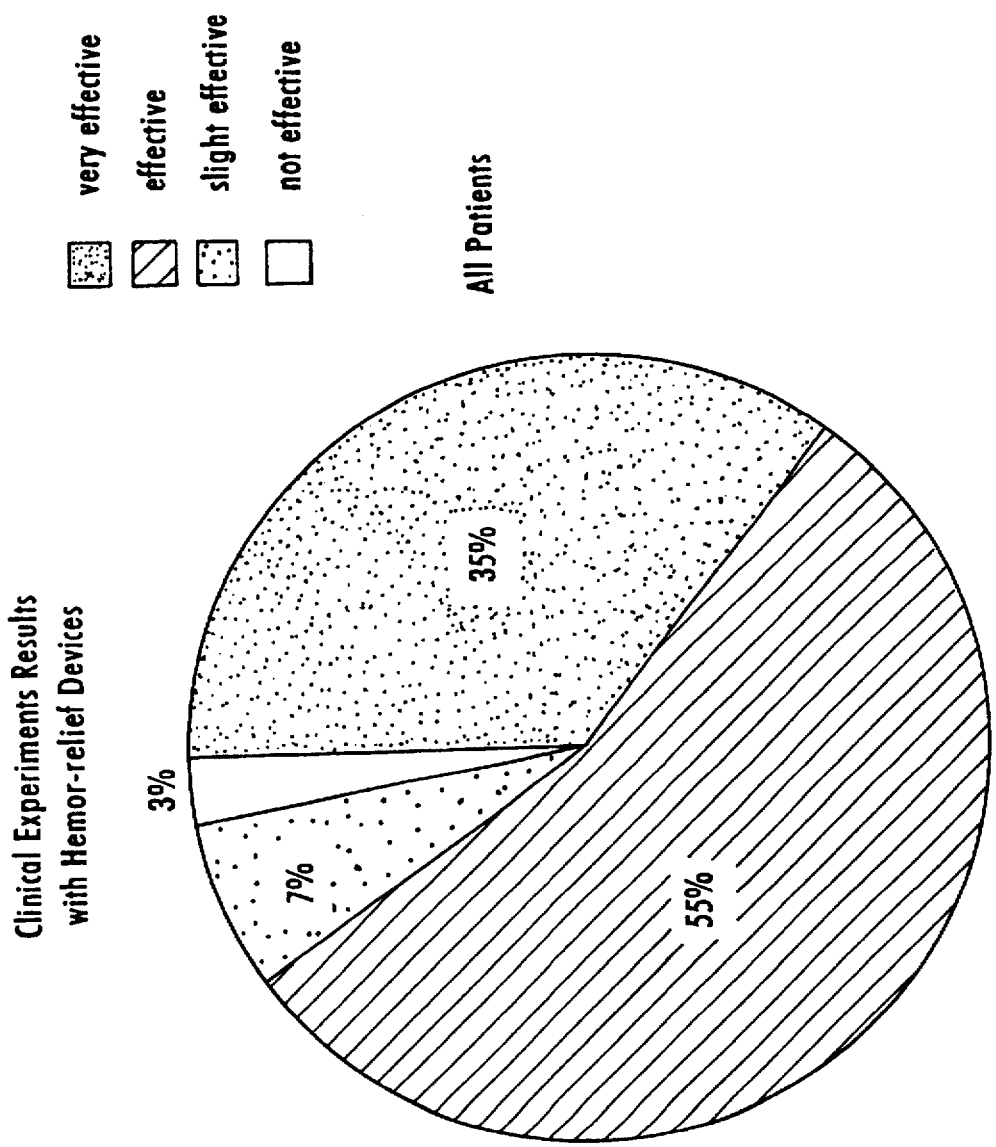
Figure 17:
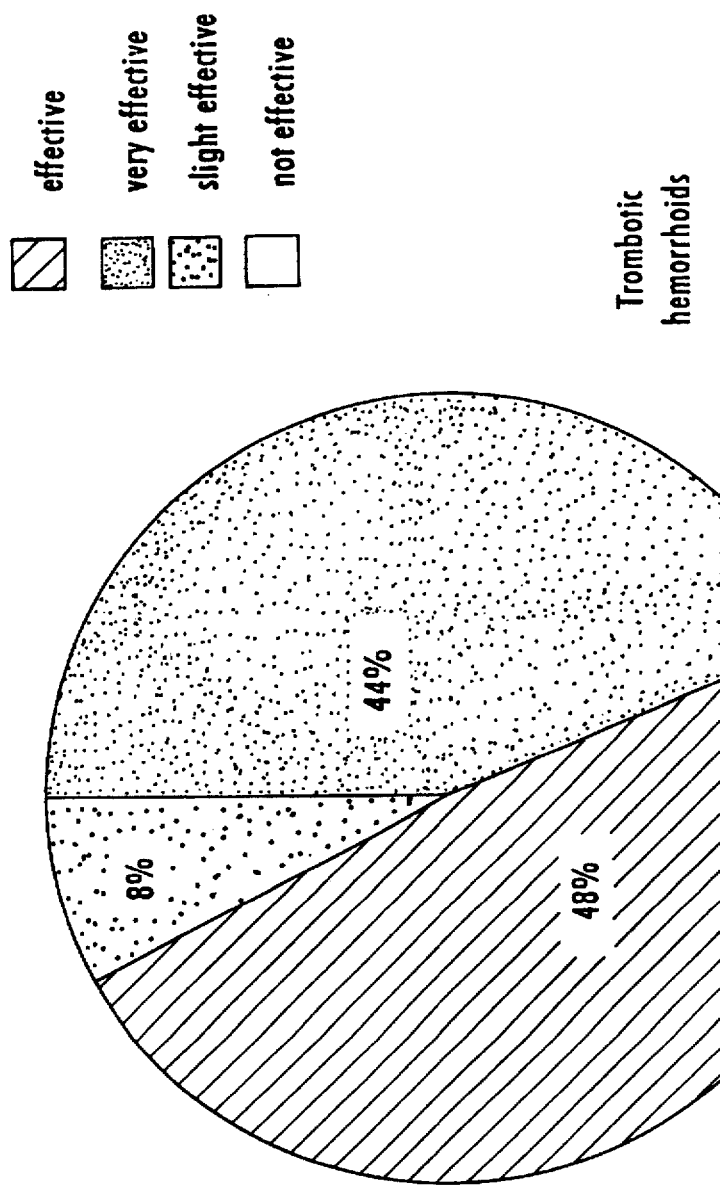
Figure 18:
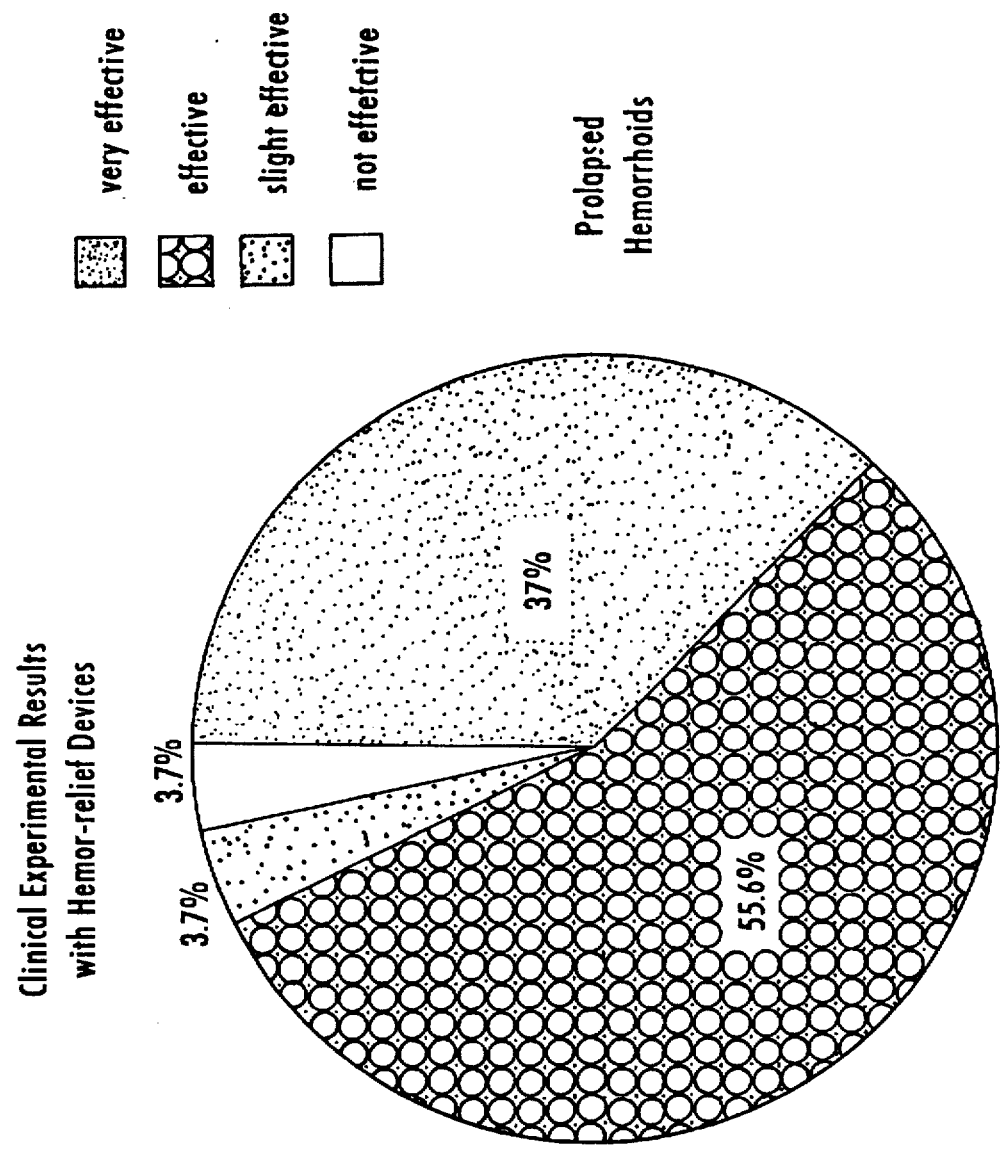
Figure 19:
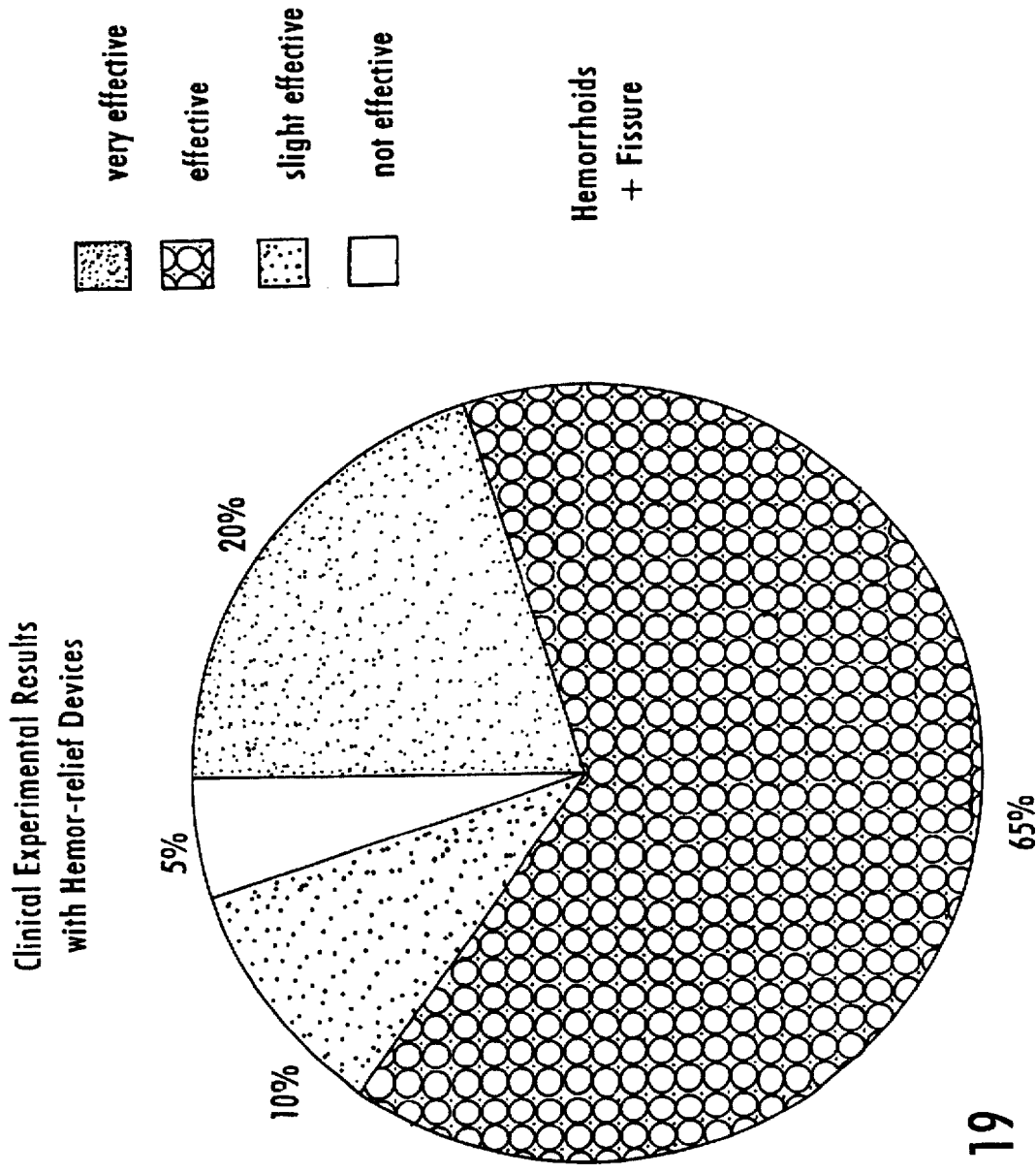

FIG. 11 illustrates a curve of temperature versus time as results of experiments made by the cylinder cooled by pumping cold water using rectal environment simulation and a sheep rectum. The curves show the comparison of the results derived by using pumping ice cold water by a pump and by gravitation as well as by using attachment of ice cold water compartment, and the present commercial "Hemorride."

The results show that the commercial cylinders used now are very limited in their effect of lowering the temperature in the rectal medium. These cylinders reduce the temperature for only one and a half minutes. Then the temperature reaches 37 degrees centigrade.

All the cylinders equipped with continuous flow of ice cold water or holding ice-cold water in a container of 240 ml attached to the insert, reduce the temperature in the rectal medium from 37° C. to under 25° C. within one minute. The temperature is still continuing to go down under 20° C. within two minutes.

The results show that the faster the flow of cold water through the cylinder, the faster the temperature decrease rate. Stainless steel cylinder is more effective in lowering the temperature than the plastic one.

Cryothermic Treatment for Hemorrhoids in Patients

Within the framework of this invention, 71 patients have been treated and the effects of the treatment were evaluated clinically.

The subjects were divided into three categories, as follows:
a. Trombotic external hemorrhoids.
b. External bleeding hemorrhoids.
c. Hemorrhoids with fissure—these hemorrhoids are classified as grade 3.

Two devices were tested. The first, a clinical model employing continuous flow to cool the treatment probe (with pump). The second, a home personal model with the probe cooled with an ice pellet. The majority of treatments were carried out using the clinical continuous model, with a few patients were treated with the home personal model.

The number of treatments varied between one and four per patient, with 90% of the subjects being treated 2–3 times. The number of treatments was determined primarily according to the severity of the condition, but also by the ability of the patients to arrive to the hospital for treatment.

The duration of each treatment session was 10 minutes at temperatures between 7–10 degree Celsius, successive treatments administered at 2 to 3 day intervals.

The patients were sent to the unit for treatment from the emergency room of from proctological clinics in the Beer Sheva area (Israel). Their ages ranged from 20 to 75 years, with 75% between 25–50 years old. The number of males and females treated was approximately the same: 38 males to 33 females.

The patients were interviewed within a short period after the treatment, and again several months later by telephone, to obtain information on the condition of the hemorrhoids, on any side effects which might have developed and the degree satisfaction from the treatment.

FIGS. 12–19 summerized the clinical experimental results.

Results

1. More than 92% of the subjects suffering from trombotic or from prolapsed hemorrhoids, and 85% of the subjects treated for hemorrhoids with fissures reported that the treatment was effective i.e. that their hemorrhoids were less painful and that the treatment reduced the odema and bleeding from the levels they previously experienced.

Objectively, the size of the trombotic hemorrhoids decreased significantly as can be seen in 25 photograhs taken before and after treatment.

2. No detrimental side effects due to the treatment were noted. In fact 95% of the subjects reported that they perfered the crythemic treatment over alternative treatment.

Conclusions

After 10 months of using the cryothemal device to treat patients suffering from hemorrhoids, it can be concluded that it is a very promising mode of treatment. It is well tolerated by the patient and is effective in reducing pain, swelling and bleeding.

On the basis of the results we believe it to be particulary effective in patients suffering from trombotic and from prolapsed hemorrhoids and somewhat less in the case of patients suffering from hemorrhoids with fissures.

In some cases the relief patients obtained immediatley enable them to resume normal functioning. In other cases it enabled us to postpone surgery for up to 3 months.

We claim:

1. A hemorrhoid therapeutic treatment system for removal of pain and therapeutic treatment of hemorrhoids and anal fissures comprising a hollow insert shaped for insertion into the anus and having an upper base formed with at least one inlet opening and at least one outlet opening, at least one inlet tube connected to said inlet opening, at least one outlet tube connected to said outlet opening, and a first container adapted to contain a cold liquid for cold liquid circulation starting from the first container through the inlet tube into the inlet opening of the hollow insert and wherein the liquid is driven back through the outlet opening of the hollow insert and through the outlet tube to a second container operated by gravity, wherein the containers are plastic containers of the sort that are commonly used for medical infusions and wherein the hollow insert terminates in an insulated tip, separated from the cold liquid, for support and insulation.

2. A hemorrhoids therapeutic treatment system for removal of pain and therapeutic treatment of hemorrhoids and anal fissures comprising an insert, shaped for insertion into the anus, fabricated using a thermally conductive material; and a thermoelectric cooler component connected to said insert, wherein the insert terminates in an insulated tip, separated from the cooler component, for support and insulation.

3. The treatment system of claim 2, wherein said insert is a substantially solid, non-hollow member.

4. The treatment system of claim 3, wherein said insert is configured without fluid circulation passages to thereby operate under the influence of said cooler component.

5. A hemorrhoid therapeutic treatment system for removal of pain and therapeutic treatment of hemorrhoids and anal fissures according to claim 2, wherein the thermally conductive material is selected from the group consisting of copper, stainless steel, titanium, nickel, chromium coated iron, and gold alloy.

6. A hemorrhoids therapeutic treatment system for removal of pain and treatment of hemorrhoids and anal fissures comprising a container adapted to contain compressed gas, a tubing connected at one end to said container, a hollow insert shaped for insertion into the anus, said hollow insert being equipped with an inlet for gas entrance into the insert and an insulated tip, separated from the compressed gas, for support and insulation, said tubing connected at a second end to the inlet, resulting in the container being connected to the insert, the compressed gas flowing into and expanding inside the insert.

7. The treatment system of claim 6, further comprising a compressed gas within said container.

8. A hemorrhoids therapeutic treatment system for removal of pain and therapeutic treatment of hemorrhoids and anal fissures according to claim 6 wherein the hollow insert has an inner diameter of approximately 1–10 mm and an outer diameter of approximately 4–13 mm.

9. A hemorrhoids therapeutic treatment system for removal of pain and therapeutic treatment of hemorrhoids and anal fissures comprising an insert shaped for insertion into the anus, an uncooled tip for support and insulation, said tip attached to said insert at a first end used for insertion, said insert cooled by direct touch with a cooling substance, wherein the insert is connected to a cup-like compartment at a second end opposite the insertion end, said compartment is covered by insulation, a removable cap adapted to attach to the compartment, a spring and piston attached to the cap and adapted to fit inside the compartment, the spring and piston adapted to press the cooling substance toward the front walls of the compartment.

10. A hemorrhoids therapeutic treatment system for removal of pain and therapeutic treatment of hemorrhoids and anal fissures according to claim 9, wherein the insert is made of aluminum, copper, stainless steel, titanium, nickel, chromium coated iron, gold alloy, or alloys thereof.

11. A cooling cylindrical device for removal of pain and therapeutic treatment of hemorrhoids and anal fissures according to claim 9, wherein the compartment is made of an aluminium, stainless steel, titanium, copper, nickel, chrominium coated iron, gold alloy, or alloys thereof.

12. A hemorrhoids therapeutic treatment system for removal of pain and therapeutic treatment of hemorrhoids and anal fissures according to claim 9, wherein the insert tip is made of an aluminium, stainless steel, titanium, copper, nickel, chrominium coated iron, gold alloy, or alloys thereof.

13. A hemorrhoids therapeutic treatment system according to claim 9, wherein the compartment having about 200 to 400 ml internal volume.

14. A hemorrhoids therapeutic treatment system according to claim 9, wherein the compartment is coated by sponge polyurethane insulation.

15. A method for using a hemorrhoids therapeutic treatment system for removal of pain and therapeutic treatment of hemorrhoids and anal fissures comprising an insert shaped for insertion into an anus, said insert having an uncooled tip for support and insulation, said insert cooled by direct touch with a cooling substance, and wherein the insert is further connected to an insulated cup-like compartment, a removable cap adapted to attach to the compartment, a spring and piston attached to the cap and adapted to fit inside the compartment, the spring and piston adapted to press the cooling substance toward the front walls of the compartment, a cylinder adapted to be removable from a base, said cylinder adaptable to fit inside the cup-like compartment, the method for treatment of hemorrhoids with a device comprising the steps of:

a) putting the cylinder onto its base, filling it with water and leaving it in a freezer to freeze;

b) separating the cylinder from its base and inserting it into the compartment;

c) screwing the cap with its spring inside by pressing it on the ice packed in the cylinder;

d) inserting the insert into the anus and holding it in place for approximately 10 minutes;

e) removing the insert from the anus.

16. A method for using a hemorrhoids therapeutic treatment system for removal of pain and therapeutic treatment of hemorrhoids and anal fissures comprising an insert shaped for insertion into an anus, said insert cooled by direct touch with a cooling substance, said insert connected to a cup-like compartment at one end, a removable cap adapted to attach to the compartment, the method for treatment of hemorrhoids comprising the steps of:

a) filling said cup-like compartment with a cooling substance;

b) placing the cap on the compartment to contain the cooling substance;

c) inserting the insert into the anus and holding it in place;

d) removing the insert from the anus.

17. A method for using a hemorrhoids therapeutic treatment system for removal of pain and therapeutic treatment of hemorrhoids and anal fissures comprising a hollow insert shaped for insertion into an anus, said insert having at a base end at least one inlet port and at least one outlet port, said insert cooled by the introduction of a cooling liquid from a first container into an inlet port, said cooling liquid exiting an outlet port into a second container, the method for treatment of hemorrhoids comprising the steps of:

a) filling a first container with cooling liquid;

b) connecting the first container to the inlet port of the insert;

c) connecting a second container to the outlet port of the insert;

d) positioning the container such that the relative height of the first container is higher than the second container, permitting the cooling liquid to flow from the first container, through the insert, and continue into the second container, utilizing only the force of gravity;

e) inserting the insert into the anus and holding it in place;

f) removing the insert from the anus.

18. A hemorrhoid therapeutic treatment system for removal of pain and therapeutic treatment of hemorrhoids and anal fissures comprising an insert, shaped for insertion into the anus, and fabricated using a thermally conductive material, said insert being connected to a source of thermoelectric energy and being internally configured to convey thermo-electrically induced conductive temperature changes to surrounding tissues, wherein said insert terminates in an insulated tip, separated from the source of thermoelectric energy, for support and insulation.

19. A hemorrhoids therapeutic treatment system for removal of pain and therapeutic treatment of hemorrhoids and anal fissures comprising a hollow insert shaped for insertion into the anus and having an upper base formed with at least one inlet opening and at least one outlet opening, at least one inlet tube connected to said inlet opening, at least one outlet tube connected to said outlet opening, and at least one container for cold liquid circulation starting from a first container adapted to contain a cold liquid through the first inlet tube into an inlet opening of the hollow insert and wherein the liquid is driven back through the outlet opening of the hollow insert and through the outlet tube to a second container operated by gravity and wherein the hollow insert terminates in an uncooled tip for support and insulation.

20. The treatment system of claim 19, wherein said uncooled tip is a thermally insulated tip to prevent thermally conductive induced temperature changes of healthy tissues in contact with said tip so that only hemorrhoids are subjected to thermal change induced by said insert.

21. An insert for use in a hemorrhoids therapeutic treatment system, comprising an insert shaped member shaped for insertion into the anus, said member being configured with a thermally conductive outer wall subjected to thermal changes occurring within said insert to transmit one of heat and cold to body tissues surrounding said outer wall; and said insert shaped member further including a thermally insulated tip at a terminal end thereof to prevent thermally conductive induced temperature changes of healthy tissues in contact with said tip so that only hemorrhoids and diseased tissues are subjected to thermal change induced by said outer wall and not said tip.

* * * * *